(12) United States Patent
Barathur et al.

(10) Patent No.: US 8,394,759 B2
(45) Date of Patent: Mar. 12, 2013

(54) TRANSDERMAL DELIVERY OF MEDICAMENTS WITH COMBINATIONS OF CETYLATED FATTY ESTER PENETRANT COMPLEXES

(75) Inventors: Raj R Barathur, Escondido, CA (US); Jack Bain Bookout, San Diego, CA (US)

(73) Assignee: Cymbiotics, Inc., Escondido, CA (US)

( * ) Notice: Subject to any disclaimer, the term of this patent is extended or adjusted under 35 U.S.C. 154(b) by 534 days.

(21) Appl. No.: 12/608,963

(22) Filed: Oct. 29, 2009

(65) Prior Publication Data

US 2011/0065627 A1      Mar. 17, 2011

Related U.S. Application Data

(60) Provisional application No. 61/116,750, filed on Nov. 21, 2008.

(51) Int. Cl.
*A61K 38/00* (2006.01)
*A61K 8/92* (2006.01)

(52) U.S. Cl. .......................................... 514/1.1; 514/63
(58) Field of Classification Search ........................ None
See application file for complete search history.

(56) References Cited

U.S. PATENT DOCUMENTS

2003/0153620 A1 * 8/2003 Meakin et al. ................ 514/552

\* cited by examiner

*Primary Examiner* — Blessing Fubara
*Assistant Examiner* — Jennifer Berrios

(57) ABSTRACT

This invention describes a topical delivery mechanism that contains a mixture of cetylated fatty esters that act as transdermal carriers of desired therapeutic molecules. The proposed cetyl fatty ester penetrant-complex (Base CFEP-complex) contains specific cetyl fatty esters, polar solvents, a carrier base (gel, cream, lotion, patch or stick gel), antioxidants and the desired pharmaceutical, cosmetic or antigenic response eliciting molecules that are efficaciously delivered by selectively varying component ratios in the complex. The invention proposes the use of transdermal delivery of medications such as those used in treatment of urinary incontinence, testosterone deficiency, arthritic and joint pain and other pains such as pain in the neck, lower back, back, knees, headaches, and other types of inflammatory pains, peripheral neuropathic pain, pain associated with repetitive strain injuries such as myofacial pain, rapid treatment of epileptic seizures, soluble antigens in the immuno-therapeutic treatment of allergies, actives in the treatment of foot cracks and elbow cracks, actives in the treatment of facial and other wrinkles in the form of anti-aging creams and gels and other topically delivered therapies.

17 Claims, No Drawings

TRANSDERMAL DELIVERY OF MEDICAMENTS WITH COMBINATIONS OF CETYLATED FATTY ESTER PENETRANT COMPLEXES

BACKGROUND OF THE INVENTION

1. Field of the Invention

The present invention relates in general to the field of transdermal and dermal drug delivery by using formulations of said compositions including chemical penetrants molecules, polar solvents, cream base, antioxidants and therapeutic pharmaceutical or cosmetic active agents for treating various diseases, pains, skin conditions and other neurological and non-neurological maladies.

In particular, the present invention relates to the formulation of a cream, gel, lotion, patch or spray (transdermal carrier) with a Chemical Penetration Enhancer (CPE) comprising of a mixture of cetylated fatty acid esters and polar solvents (Cetylated Fatty Ester Penetrant Complex; CFEP-complex), in predetermined combinations and with desired pharmaceutical and cosmeceutical agents, which when added together in the vehicle carrier and administered to the skin of an individual has the effect of carrying the therapeutic substance across the skin barrier and enabling the dermal and/or systemic beneficial effects of the transported molecules.

2. General Discussion and Related Art

Transdermal Drug Delivery (TDD) and Approaches to Permeation Most transdermal drug delivery inventions can be divided into system innovations and formulation innovations. The system innovations involve mainly technologies that use either mechanical or various energy sources to increase drug flux across the skin. Formulation innovations involve chemical systems that either attempt by various alterations at the molecular level to increase the flux of drug across the skin or improve performance and stability of a Transdermal Delivery (TDD) system.

Gels, creams, lotions, and sprays, for which many chemical system innovations have been developed, have a long history in topical and local dermal applications. There are many advantages for the mode of application: convenience of application, numerous potential sites of application, demonstrated dosing potential in multiple formulations with reasonable safety, and a potentially larger surface area for application than a transdermal patch.

The major steps in transdermal permeation are: 1) partitioning of the permeant in the outermost layer of the stratum corneum (with keratin-filled corneocytes anchored in a lipophillic matrix), 2) diffusion after partitioning through the stratum corneum, then 3) further partitioning at the stratum corneum/viable epidermis junction as the permeant diffuses through the junction into viable tissue and 4) partitioning and diffusion through the dermal tissues into the capillaries. Further effects on the partitioning and diffusion processes are the binding of permeants to various elements (such as binding to keratin or drug receptors) of the skin (reservoir effect) and metabolic effects on the permeant that may occur during the process of permeation. By these latter effects permeants may become degraded or activated (i.e, prodrug converted to drug by activation metabolism).

By "transdermal" drug delivery is meant administration of a drug to the skin surface of an individual so that the drug passes through the skin tissue and into the individual's blood stream.

The term "topical administration" is used in its conventional sense to mean delivery of an active agent to a body surface such as the skin or mucosa, as in, for example, topical drug administration in the prevention or treatment of various skin disorders, the application of cosmetics and cosmeceuticals (including moisturizers, masks, sunscreens, etc.), and the like. Topical administration, in contrast to transdermal administration, provides a local rather than a systemic effect.

Similarly, when the term "transdermal" is used herein, as in "transdermal drug administration" and "transdermal drug delivery systems," it is to be understood that unless explicitly indicated to the contrary, "topical" administration and systems are intended as well.

Advantages of transdermal delivery include: avoidance of first pass effects described for tablets and capsules; and problems associated with stomach irritation. In certain circumstances, it is desirable to deliver a therapeutic agent or cosmetic agent topically to the skin at a target site. Both transdermal and topical delivery devices rely on the adherence of a cream, gel, lotion, spray or a patch to the surface of the skin or other body surface.

Chemical Permeation Enhancers (CPE)

Approximately 450 chemicals are classified as Chemical Permeation Enhancers (CPE). CPEs are typically classified under (1) Water (2) Sulfoxide (3) Azone (4) Pyrrolidones (5) Fatty Acids (6) Alcohols, Fatty Alcohols and Glycols (7) Surfactants (8) Urea and (9) Essential Oils, Terpenes and Terpenoids.

Depending on their mechanism of action, CPEs can also be divided in 2 broad categories—either those that alter the structure of the skin lipids, thereby decreasing their resistance to diffusion (e.g., Polyethylene Glycol, alcohols and Menthol) or those that enhance the solubility of the diffusing drug within the skin.

CPEs may facilitate delivery by combinations of the following mechanisms: displacement of bound water, loosening of the corneocyte polymeric structure, extraction of lipids from the stratum corneum and inducing delamination of the stratum corneum osmotically, causing swelling and inducing channels to form in the matrix.

CPEs can increase entropy (As) in the lipid bilayers, thus reducing the skin barrier to diffusion, allowing topically applied drugs to diffuse through more easily. They operate in complex interacting ways to change the intercellular region of the horny layer of fluidization altering polarity, phase separation, or lipid extraction.

Innovations of the present invention address permeation of both lipophilic and hydrophilic compounds:

Lipophilic compounds partition into and penetrate the lipid domains of the stratum corneum. Hydrophilic compounds and ionized species require different approaches to penetration than that of uncharged lipophilic chemicals. Unlike lipophilic compounds, polar compounds demonstrate permeability coefficients that suggest independence of lipophilicity in order to penetrate. In general, permeability coefficients for ionized compounds are lower than coefficients for nonionized compounds because of higher water solubility. Further, permeability may show additional complexity when both ionized and nonionized species are simultaneously penetrating the skin (for example, partially ionized chemicals such as atropine, naproxen and salicylic acid).

Fatty Acids in Transdermal Delivery

A wide variety of long-chain fatty acids, which have been used as CPEs, increase transdermal delivery; the most popular being oleic acid (C18 unsaturated), followed by linoleic acid (C18 polyunsaturated). Fatty acids effects on drug delivery to and through human skin can vary. It is relevant that many penetration enhancers contain saturated or unsaturated hydrocarbon chains and some structure-activity relationships have been drawn from the extensive studies.

Various analogs of fatty acids have been researched as penetration enhancers, for example diesters increased the permeation of NSAIDS through rat skin [Takahashi, K et al 2002 Drug Dev Ind Pharm 28:1225]. In addition, fatty acids have been shown to improve percutaneous absorption of, among others, estradiol, progesterone, acyclovir, 5-fluorouracil, and salicylic acid, which indicates that these CPEs can be used to promote delivery of both lipophilic and hydrophilic permeants. It is this property of facilitating both types of permeants that makes fatty acids desirable as enhancers. U.S. Pat. No. 4,940,586 discloses skin permeation enhancement due to fatty acid sucrose esters. U.S. Pat. No. 5,006,342 lists numerous fatty acid esters or fatty alcohol esters, for which the fatty acid/alcohol portion are about 8-22 carbon atoms. U.S. Pat. No. 4,863,970 describes a penetration-enhancing vehicle containing one or more cell-envelope disordering compounds such as oleic acid, oleyl alcohol (and others) in an inert diluent, such as water.

Extensive studies on a range of fatty acids and alcohols, sulfoxides, surfactants, and amides as enhancers for naloxone by Aungst and coworkers [Aungst, et al 1986 Int J pharm 33:2256; Aungst et al 1989 Pharm Res 6:244] showed that saturated acids with a chain length of C9-C12 increased the flux of the drug 40-fold, whereas unsaturated fatty acids required optimum chain length near C18: for example oleic acid and linoleic acid.

Related experiments have demonstrated that saturated alkyl chain lengths of around C10 to C12 attached to a polar head group yield the best promoters. Hydroxylated and esterified derivatives of various fatty acids, such as cis-9-octadecenoic acid (oleic acid), cis-(ricinoleic acid) and trans-(ricinaelaidic acid), have also been synthesized and studied for permeation enhancement of hydrocortisone and 5-FU in vitro, by using excised hairless mouse skin [Song et al 2001 Int J Pharm (amst) 212:153-160].

It is apparent from numerous literature reports that the fatty acid derivatives interact with and modify the lipid domains of the horny layer as would be expected for a long chain fatty acid with cis configuration. Spectroscopic investigations using deuterated oleic acid in human stratum corneum indicates that at a higher concentration, it can also exist as a separate phase within the bilayer lips [Takahashi, K et al 2002 Drug Dev Ind Pharm 28:1225]. The creation of such pools provides permeability defects within the intercellular domain thus facilitating penetration of hydrophilic permeants through the membrane.

Description of Cetylated Fatty Esters as CPEs in the Disclosed Invention

The present invention relies greatly on cetylation of the desired fatty acid esters to facilitate permeation and thus the delivery of the desired therapeutic molecule or molecules. The presence of the cetyl chain greatly increases the molecular size of the esterified molecules, as well as providing additional lipophilic characteristics due to the hydrocarbon chain. This portion of the CPE molecule presents the least disruption of the lipid matrices in the stratum corneum and facilitates penetration. A graphic depiction showing an example of an esterified fatty acid is shown below

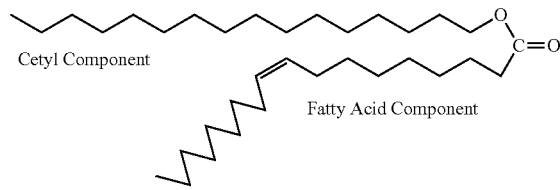 [SMILES: CCCCCCCC/C=C\CCCCCCCC(=O)OCCCCCCCCCCCCCCCC]

Fatty acids that are alkanes with no unsaturated regions provide secondary structure that is straight and that can readily intercalate between membrane lipids with least disruption. Fatty acids with double bonding between carbons in a cis configuration introduce bending in the secondary structure that when intercalated in the membrane lipids, causes disruptions in the membrane configuration. Likewise, branching of the fatty acid carbon chain or with the introduction of cis-unsaturation, chain branching, or methyl or methoxy-groups along the fatty acid carbon chain can be utilized. These molecules intercalate within the lipid bilayers with several disruptions—rotating, vibrating, translocating, forming microcavities and increasing the free volume available for drug diffusion. Pooling may occur with formation of permeable pores that, for polar molecules, provide greater access to viable epidermis. This may be a critical step in allowing diffusion through the gel-like viscosity of the lipid matrix.

Background of Targeted Maladies

Testosterone Deficiency

Hypogonadism is a significant problem and these patients suffer from testosterone deficiency. In the United States there are an estimated 10 to 11 million patients who suffer from testosterone deficiency. Testosterone Replacement Therapy (TRT) has been around for a long time and there are various options available for TRT.

Intramuscular injections: These injections are given once every 10 to 14 days, and contain testosterone in various forms such as testosterone enanthronate, testosterone propionate, testosterone cypionate and testosterone undecanoate. Patients find these injections painful and uncomfortable and affective for up to 10 days Oral Testosterone: Is not very effective and these oral compositions may contain mesteroline, testosterone undecanoate, methyltestosterone, and fuoxymesterene.

Transdermal Delivery:

Subcutaneous: This is not such a common method but pellets containing Testosterone are placed subcutaneously.

Transdermal: There are two main ways, one using a transdermal patch and the second using a gel. There are several of these products on the market such as Androgel (Unimed Pharmaceuticals), Testogel (Bayer Pharmaceuticals), Testim (Auxilium Pharmaceuticals) and Andractim (Laboratories Besins-Isvesco, France). All of these are 0.7% to 1% testosterone gels. This has to be applied everyday. The delivery mechanism of the gel resides in testosterone drying up on the skin and being absorbed by the skin continuously.

The current invention proposes to deliver these molecules transdermally using the CFEP carrier.

Urinary Incontinence UI: Urinary Incontinence UI affects about 15% of the population particularly women—most especially after women have had two-three children. An estimated 20-25% of the women over age 50 have UI. There are 17 million men and women in the USA suffering from UI. Out of the two most common treatments, oral Oxybutynin is more effective than oral Tolteridone, but the former carries more significant side effects. Although both molecules are effective in the treatment of UI, the associated side effects result in poor patient compliance with continuing the oral treatment. A major side effect is extreme drying of the mouth which in turn results in need to drink a lot of water and thus results in urge to void. Oxybutynin also enters the blood brain barrier and thus has been shown to have some cognitive impairment. Constipation, sweating and drowsiness are other side effects reported. Oxybutynin is metabolized very quickly in the liver and thus the side effects are less in orally administered Tolteridone but drying of mouth is common in both modalities. Patient compliance is ~30% with oral Oxybutynin and around 40-50% with Tolteridone. There are 2 treatment options available: Oral tablets or Transdermal Patches 1. Oral Tablets: There are 2 compounds currently available worldwide and they are Oxybutynin and Tolterodone. Oxybutynin is a Muscarinic receptor antagonist. When patients take these formulations, they act on smooth muscles inhibiting acetylcholine thus increasing bladder capacity by reducing the number of motor impulses to void.

2. Oxybutynin Patches: Oxytrol is a transdermal patch available on the market manufactured by Watson Pharmaceuticals. This is effective and the side effects seen with orally administered Oxybutynin are minimized.

The current invention proposes to deliver these molecules transdermally using the CFEP carrier.

Musculoskeletal pain, joint pain and other types of inflammatory pain: Arthritis is a disease which affects approximately one in seven Americans, and which actually encompasses more than one hundred different diseases frequently having entirely different symptoms, causes, and known treatments.

Cetyl myristoleate has been used for treatment of rheumatoid arthritis (Diehl, U.S. Pat. No. 4,113,881) and osteoarthritis (Diehl, U.S. Pat. No. 5,569,676) [Hesslink et al. 2003, Kramer et al. 2004]. Other types of pain include repetitive strain injuries (a subcategory of Myofascial pain syndromes) tendonitis, bursitis, lower back pain, neck pain, fibromyalgia pain and headaches (Sharan D, et al. 2009, submitted for publication.

The current invention proposes to deliver these molecules transdermally using the CFEP carrier.

Neuropathic Pain (NP): Approximately 4 million individuals in the United States alone suffer from Neuropathic Pain (NP) such as pain seen in patients with diabetes (Diabetic peripheral neuropathy), Bell's palsy and Post Herpetic Neuropathies. Furthermore, NP response to traditional analgesics has been found to be relatively poor and oral treatments often do not provide instant pain relief as the drugs administered needs time to work on the targeted pain pathways.

Oral tablets containing methylcobalamin have been used in treating patients with Vitamin B12 deficiency, pernicious anemia and neuropathic pain in diabetics and other disorders. Vitamin B12 is absorbed very slowly and its positive effects are slow to act in patients with Diabetic Peripheral Neuropathy. Thus pain relief may be slower to attain. Sublingual methylcobalamin administration is a new approach for which there are claims for rapid absorption through the pores beneath the tongue. Sublingual administration is widely used by doctors in the treatment of Vitamin B 12 deficiency, pernicious anemia and neuropathic pain. Oral methylcobalamin is absorbed by passive diffusion at a rate of 1-2% of the ingested material. Food bound B12 malabsorbtion is common especially in older people. Cyanocobalamin is also administered using intravenous and nasal routes but the compliance is poor.

An alternative way to administer the methylcobalamin is through the transdermal route and in the form of a cream or gel or spray or a patch. There are several advantages of transdermal delivery as it avoids being metabolized in the liver, increases patient compliance, and most importantly the dosage used in oral formulations can be reduced significantly. US PTO#20080233180 (provisional) describes the delivery of methylcobalamin via skin patches using methylene and propylene glycol. Methylcobalamin molecule is large (MW 1355) and may be considered not possible to penetrate the skin, because only molecules less than 350 MW or lower can penetrate the skin. In our invention we have shown that CFEP carriers appears to facilitate penetration methylcobalamin rapidly. The current invention proposes to deliver these molecules transdermally using the CFEP carrier.

Pregabalin and gabapentin oral tablets or capsules have been used in the treatment of convulsions and seizures and more recently in treating neuropathic pain and fibromyalgia. The US FDA has approved a drug under the brand name of Lyrica marketed by Pfizer. Although an effective formulation the oral formulations are associated with adverse reactions such as drowsiness and dizziness in more than 10% of the patients. In addition a large number of patients report visual disturbance, lethargy, memory impairment, erectile dysfunction and weight gain. Oral Pregabalin is rapidly absorbed with bioavailability of more than 90%. Pregabalin greatly potentiates benzodiazepan and barbiturates and other depressants and may cause dependence and abuse. The current invention proposes to deliver pregabalin and gabapentin molecules transdermally using the CFEP carrier in order to obviate the dependence and maybe reduce the significant side effects.

Repetitive Strain Injuries (RSI): RSI is a multifactorial pain syndrome affecting the neck, upper back, shoulder, upper and lower arm, elbow, wrist or hand, or a combination of these areas, which leads either to impairment or to participation problems. The syndrome is characterized by disturbance in the balance between load and physical capacity, preceded by activities that involve repeated movements or prolonged periods spent with one or more of the relevant body parts in a fixed position as one of the presumed etiological factors. Typical manifestations include tightness, discomfort, stiffness, soreness, tingling, loss of strength and coordination in arms, pain in upper neck, back, lack of sleep due to pain and others. In general, RSI include more than 100 different kinds of disorders usually arising due to a combination of physical and psychosocial factors. These injuries vary from person to person in type and severity. An estimated 20-30% of software engineers and client service representatives suffer from these injuries. Several NSAIDS with or without physical therapy are used in treating such patients. Similarly a complex of fatty acid esters have been used in treating such pain transdermally (Sharan et al., 2009, submitted for publication). The current invention proposes to deliver these molecules transdermally using the CFEP carrier.

Hyperkeratosis and Xerosis: Otherwise known as cracked feet, it affects 20-30% of the normal population and at least 30% of patients who have chronic diabetes. Untreated, cracked feet in diabetics are prone to ulceration, which may get infected and in severe situations require amputation. Xerosis can be defined as dehydration of skin characterized by redness, dry scaling, and fine cracking much like the cracking of porcelain. Xerosis occurs most frequently on the extremities, especially the feet and legs. Hyperkeratosis is usually defined by monitoring the hypertrophy of the horny layer of the skin. This contributes to the flattened and raised borders noted in severity descriptions. Several alpha hydroxy acids have been used in the treatment of Xerosis. The current invention proposes to deliver these molecules transdermally using the CFEP carrier.

Epilepsy:

A great amount of empirical research has been conducted to treat the various subtypes of epilepsy. Status Epilepticus (SE) is typically treated with valproate, phenytoin, thiopentone, pentobarbital, propofol, isoflurane, felbamate, midazolam, diazepam, clobazam, folinic acid, pyridoxine, gabapentin, or vigabatrin. For refractory generalized convulsive status epilepticus, continuous intravenous midazolam infusion at 0.1-0.6 mg/kg/hr after a 0.2 mg/kg intravenous bolus is effective and has advantages over traditional therapies since it induces less hypotension and cardio-respiratory depression and can be easily titrated; cessation of seizures usually occurs before burst suppression is achieved on EEG.

Diazepam is commonly used as a first treatment for SE and acute seizures, and is restricted to patients with continuing convulsions or those having another convulsion during infusion of a maintenance medication. Lipid soluble Diazepam enters the brain rapidly, and provides an anticonvulsant effect shortly after administration. Although diazepam is a drug of choice for the management of refractory SE, the longer duration of action of lorazepam and clonazepam may favor the use of these latter two drugs.

Typically 10 mg of diazepam (0.15 mg/kg) is administered intravenously over a period of a few minutes. Diazepam administration can also be in a buccal or rectal formulation. Rectal and buccal formulations bypass metabolism in the liver and diazepam is in the system within 30 to 40 minutes. Compared to rectal and buccal administration, intramuscular and oral diazepam are metabolized slowly and is not used when acute seizure control is needed. The current invention proposes to deliver these molecules transdermally using the CFEP carrier.

SUMMARY OF THE INVENTION

It is therefore an object of the present invention to describe newly discovered and proposed benefits of a transdermal delivery formulation of carrier cetylated fatty esters. Ingredients for the formulation containing a mixture of a carrier cream comprising of cetylated fatty esters, polar solvents, excipients, and specific pharmaceutical molecule or molecules administered using the CFEP-complex in order to remedy one of the above-referenced maladies.

According to a broad aspect of the invention, described is a composition of a transdermal delivery mechanism that contains a complex of selected cetylated fatty acid esters that act as better penetrants in delivering pharmaceutical molecules, nutraceuticals, cosmeceuticals, and antioxidants through transdermal barriers. The composition of the invention includes penetrants as described, polar solvents, adjustment of pH for specific applications or treatment of various maladies and based on specific chemical molecules that need to be transdermally transported into the vascular system or musculature under the skin and skin layers.

The foregoing objects and advantages of the invention are illustrative of those that can be achieved by the present invention and are not intended to be exhaustive or limiting of the possible advantages which can be realized. Accordingly, the present invention resides in the novel, formulation compositions and improvements herein shown and described, or as modified in view of any variation which may be apparent to those skilled in the art.

DETAILED DESCRIPTION OF THE INVENTION

Definitions, Nomenclature and Terminology

In describing and claiming the present invention, the following terminology will be used in accordance with the definitions set out below.

1. "Active agent" is used herein to refer to a chemical material or compound suitable for administration to a human patient and that induces a desired beneficial effect, e.g., exhibits a desired pharmacological activity. The term includes, for example, drugs or agents that are therapeutically effective, prophylactically effective, and cosmetically (and cosmeceutically) effective. Also included are derivatives and analogs of those compounds or classes of compounds specifically mentioned which also induce the desired beneficial effect.
2. "Cosmeceuticals" are cosmetic products that are claimed, primarily by those within the cosmetic industry, to have drug-like benefits. Examples of products typically labeled as cosmeceuticals include anti-aging creams and moisturizers. The "cosmeceutical" label applies only to products applied topically, such as creams, lotions, gels, sprays and ointments. Cosmeceuticals may contain purported active ingredients such as vitamins, peptides, phytochemicals, enzymes, antioxidants, and essential oils.
3. "Diffusion" is the movement of molecules through a domain, by random molecular movement, from higher concentrations to lower concentration.
4. "Diffusion Coefficient (D)" is the diffusion coefficient of the permeant measured as area/time ($cm^2$/hr or $cm^2$/sec)
5. "Flux (J)" is the amount of permeant crossing the skin or entering systemic circulation. This is measured as mass/area/time (or ug/$cm^2$/hr).
6. "Permeant" is a molecular species moving through or moving into the tissue.
7. "Permeation" is the movement of the permeant through the membrane. Permeation includes partitioning of the permeant into various domains (e.g., keratinocytes, lipids, etc.) and diffusion through the domains.
8. "Nutraceutical" is (a) a synthetically produced bioactive compound, where no structurally identical, naturally produced analog to the synthetically produced bioactive compound exists; or (b) a biologically active compound derived from a living organism, where the biologically active compound is not a dietary supplement.
9. "Transdermal" drug delivery is meant administration of a drug to the skin surface of an individual so that the drug passes through the skin tissue and into the individual's blood stream.
10. CFE blend: This is defined as selected group of cetylated fatty acid esters combined with other molecules, which serves as the transdermal carrier of selected molecules used in the formulations for transdermal delivery of actives specific to a particular disease or diseases or cosmetic agents or other agents for non medical and non cosmetic usage.

The Invention

The present invention relies greatly on cetylation of the desired fatty acid esters to facilitate more efficacious permeation and thus the delivery of the desired therapeutic molecule or molecules. Broadly, the inventive composition is a medicinal composition containing a pharmaceutical or cosmecutical used for the treatment of a first predetermined ailment or a symptom thereof, and a cream comprising of a mixture of cetylated fatty ester carrier molecules used for transdermal and dermal delivery. The current invention provides properties that decrease diffusion resistance and enhance drug solubility.

The vehicle of interest in this invention is constituted from the combination of the polar solvent material and the polar lipid material. Both demonstrate lipophilicity and together penetrate into the stratum corneum carrying the permeant.

Preferably, the polar solvent material in this invention is propylene glycol and the polar lipid material is a combination of cetylated fatty esters (CFEs or also known as cetyl ester waxes). Other polar solvents used instead of or in conjunction with propylene glycol include glycerol, ethylene glycol, 1,2, 6-hexane triol, 1,2,4-butane triol, propylene glycol ether of methyl glucose or sorbitol, dimethicone copolyol, and polyethylene glycol (preferably, PEG 50, PEG 100 and PEG 500). The polar solvent provides hygroscopic and miscible properties that allow solubility for the cetylated esters, which in turn serve to enhance penetration for the permeant. The behavior of propylene glycol and some of the above solvents as enhancers have been disclosed in U.S. Pat. Nos. 4,973,468, 4,006,218, 3,551,154 and 3,472,931.

Upon application of vehicle containing the permeant to the skin, the volatiles evaporate while the CFE complex allows for near-saturation concentration of the permeant on the skin without precipitating. The polar solvent and CFE complex act in conjunction to allow for rapid absorption and avoid formation of a waxy film that would slow permeant migration. The primary delivery effect of the CFE complex is that of a penetrant agent and to move other permeants through the permeation barrier of the stratum corneum to the site desired for utilization of the drug.

This invention describes the use of cetylated fatty esters. In other patents and in routine uses, cetyl ester waxes are used primarily in formulations as stiffening agents due to the semisolid characteristics of these molecules at temperatures below 40° C. While this property is useful in the formulations described for this invention, the stiffening characteristic is not part of the embodiment. A principal embodiment of this invention is to use the properties of both the cetyl and fatty acid components to act in conjunction as a penetrant agent (CPE).

The ester composition of the proposed invention is varied depending on the properties of the active ingredients in the formulation and the desired delivery effects (i.e., systemic delivery, skin delivery, or tissue delivery). The cetyl component is present with all molecules in the combination of esters used. The cetyl component facilitates entry into and through the matrix. However, the alkyl fatty acid component is variable depending on the delivery considerations or effects.

1. This component may be of simple alkyl chain length from 8 to 35 carbons, the composition of which may be saturated, mono- to polyunsaturated, or may contain functional groups such as methoxy-, amino- or ring structures.
2. This component may also be branched depending on the desired delivery effects.
3. Finally, different cetylated ester molecules may be used together to provide the desired delivery effects, influencing solubility and the solvent vehicle characteristics. An example would be the combination of cetyl 13-methyl myristate, cetyl linolenate and cetyl isolaurate together to provide increased water solubility and permeation potential for more hydrophilic drugs.
4. In some embodiments where hydrophilic properties of the drug specify, a cetylated amino ester (such as cetyl arginine and/or cetyl ornithine) is included in the mix of cetylated ester molecules.

Specifically, different cetylated ester molecules are used depending on the physico-chemical properties of the permeant; however, the combinations are all designed either to increase permeant flux for permeants where systemic or tissue delivery is desired or to retard flux in order to maintain the permeant longer within the epidermis and dermis if the skin is the target site of delivery. It is noted that the CFEs utilized in this invention have structural similarities to the ceramides (namely, a sphingoid base and a fatty acid, which are linked by an amide bond between the carboxyl group of the fatty acid and the amino group of the base) present in the stratum corneum matrix of human skin, but that the functional groups present on the fatty acid components in the CFE complex are included in the vehicle for the penetration properties desired for the invention.

The variations in the fatty acid component of the CFE complexes serve a dual role. First is the introduction of alignment flaws in the orientation of the molecules in the complex. Many fatty acids are straight-chain compounds. The hydrocarbon chains form compact orientations with hydrophilic portions compacting closely together in a lattice-like matrix. The use of cetylated forms with only saturated straight chain fatty acids results in the least disruption in alignment and least flux enhancement. Unsaturation of the fatty chain into a cis structure results in a bending of the chain that would cause disruption of the intercellular lipid packing of the stratum corneum. Introduction of a cetylated form with a single cis-unsaturation, such as a cetyl oleic ester, or a cis-unpolysaturated component, such as a cetyl linolenic ester, introduces the potential for more alignment flaws and greater flux enhancement. The variety of fatty acids introduce disruptions in the alignments and compactness of the complex and, in turn, similar disruptions in the lipid bilayers of keratinocyte and fluidization within the lipid matrix of the stratum corneum.

The second role is to introduce functional groups that have heightened affinities for the permeants of interest (i.e., functional groups with polar affinities for more ionic permeants or with more lipophilic affinities for more non-polar permeants). The structural composition of the CFE complexes is conducive for the delivery of both lipophilic and hydrophilic permeants.

1. Hydrophilic compounds and ionized species require different approaches to penetration than that of uncharged lipophilic chemicals. The cetylated molecules form complexed layering in which the permeants may become incorporated noncovalently for delivery to the skin. The invention complex partitions within the stratum and allows for diffusion of the permeant to proceed at rates mediated by the properties of the drug molecules and the composition of the cetylated complex. The cetylated complex helps to reduce water loss from the stratum corneum, increasing hydration and assisting in diffusion of more ionic permeants. The cetylated complex creates permeability by disrupting the lipid organization of the stratum corneum, increasing the diffusion coefficients of the permeants. The structure of the cetylated molecules play a major role in this process.
2. Lipophilic compounds partition into and penetrate the lipid domains of the stratum corneum. The CFE complex of this proposed invention provides more efficient penetration through its affinity for the permeant, complexing as previously noted, and partitioning into the bilayer lipids, disrupting the organized packing but also dispersing within the intercellular lipids to facilitate permeant diffusion.

In the first embodiment of the invention, a transdermal drug delivery carrier cream, gel, lotion, spray or patch that enhances transdermal drug delivery efficiency is proposed that utilizes a formulation comprising of a mixture of cetylated fatty esters and a polar solvent (called CFEP complex) in a cream base and an anti-oxidant, the permeant of interest and any additional excipients (such as fragrance, skin protectants, or colorants).

Particularly preferred formulations for topical cream Base CFEP-complex in accordance with the first embodiment of the invention include 4-20% of a penetrant in group A in a combination as listed below:

A: Penetrant Group Formula. Four or more of the following in the indicated concentration ranges:
Cetyl arginine, 0.025-2%
Cetyl 11-cyclohexylundecanoate, 0.25-2.5%
Cetyl decanoate, 0.25-2%
Cetyl dihomo-γ-linolenate, 0.25-3%
Cetyl docosapentanoate, 0.6-4%
Cetyl eicosapentanoate, 0.6-4%
Cetyl isolaurate, 0.25-3%
Cetyl isomyristate, 0.25-3%
Cetyl laurate, 0.05-1.6%
Cetyl linolenate, 0.6-4%
Cetyl 2-methoxy-5-hexadecenoate, 0.25-2.5%
Cetyl 13-methyl myristate, 0.25-2.5%
Cetyl myristoleate, 0.6-15%
Cetyl myristate, 0.75-8%
Cetyl oleate, 0.25-5%
Cetyl ornithine, 0.025-2%
Cetyl palmitate, 0.2-5%
Cetyl palmitoleate, 0.3-2%
Cetyl stearate, 0.05-1.6%
Cetyl stearidonate, 0.25-3%
Cetyl vaccenate, 0.25-3%

B: POLAR SOLVENT. One or more of the following in a combined final concentration of 5-30%:
1,2,4-butane triol
dimethicone copolyol
ethanol
ethylene glycol
glycerol
glyceryl monostearate
1,2,6-hexane triol
isopropanol
polyethylene glycol (preferably PEG 50, PEG 100 and/or PEG 500)
propylene glycol C: CREAM BASE. Depending on the permeant and the application, one of the following may be used:
a. Cream Base for pH from 5 to 8
Carbopol 940, 0.2-5%%
Cetyl stearyl alcohol 2-6.0%
Cremophor 40, 0.8-3%
Disodium EDTA, 0.1-0.3%
Methyl paraben 0.1-0.2%
Propyl paraben 0.02-0.08%
Purified Water 50-80%
Triethanolamine, pH variable concentration
b. Cream Base for pH from 2-4
Carbopol Aqua CC, 1-5%
Cetostearyl alcohol 2-6%
Dimethicone, 1-5%
Disodium EDTA, 0.1-0.3%
Glycolic acid, 5-20%
Isopropyl myristate, 1-5%
Methyl paraben 0.1-0.2%
Olive oil 1-5%
PEG-100 stearate 1-8%
Propyl paraben 0.02-0.08%
Purified water 25-40%
Triethanolamine 4-8%

D: ANTIOXIDANTS. Examples include, but are not limited to, one or more of the following in a final concentration of 1-10%:
Alkyl gallates
Alpha lipoic Acid
Ascorbic acid
Butylated hydroxyanisole
Butylated hydroxytoluene
Catechins (such as epicatechin (EC) and epigallocatechin gallate (EGCG)
Citric acid
COQ10
Curcumin
Sodium bisulfate
Sodium metabisulfate
Thiourea
Tocopherol acetate Example 1

Systemic Delivery of Oxybutynin

Oxybutynin is a muscarinic receptor antagonist used in the treatment of urinary incontinence. An active metabolite of oxybutynin, N-desethyl-oxybutynin (DES), may play major role in secondary effects such as dry mouth.

A topical application of oxybutynin was applied to the shaved skin of rabbits at concentrations of 5 mg/ml (A) or 0.5 mg/ml (B). The carrier formulation consisted of a penetrant group of 8 cetyl fatty esters (7%, cetyl decanoate, cetyl laurate, cetyl myristate, cetyl myristoleate, cetyl oleate, cetyl palmitate, cetyl palmitoleate and cetyl stearate) with propylene glycol as the polar solvent (15%), menthol (1.56%), tocopherol acetate (1%), in the described cream base at a pH of 6.0.

The application was administered once to a 40×60 mm area, the area covered (secured), and then plasma samples were taken for a 24-hour period thereafter. The results at the indicated time points are as follows, the mean plasma level at each time point representing the average of 4 animals.

TABLE 1

Dose Response in Plasma Sampling

| Time (hrs) | Mean in ng/ml | |
| --- | --- | --- |
| | A | B |
| 0 | 0 | 0 |
| 0.25 | 0.78 | 0 |
| 2 | 4.29 | 0.82 |
| 6 | 9.33 | 0.84 |
| 12 | 5.55 | 0.86 |
| 24 | 2.01 | 0 |

The plasma levels confirmed a dose response relationship and the ability of the carrier formulation to provide effective levels of oxybutynin systemically. The penetrant group was chosen for its affinity for the relatively hydrophobic permeant and for delivery efficiencies developed for systemic applications.

Although intravenous injection of oxybutynin (5 mg) renders a Tmax of 0.25 hrs, the Tmax of application A was 6 hours and an effective plasma level over most of the 24-hour observation period (Table 2). These features are attributed to the carrier formulation based on the penetrant group.

TABLE 2

Kinetics of Dosing Responses

| | A | | B | |
|---|---|---|---|---|
| | Oxybutynin | DES | Oxybutynin | DES |
| Cmax (ng/ml) | 9.33 | 0 | 0.836 | 0 |
| Tmax (hr) Approx. | 6 | 0 | 12 | 0 |
| AUC | 21.958 | 0 | 2.512 | 0 |

A second preferred penetrant group for this and similar permeant drugs is cetyl isomyristate, cetyl laurate, cetyl myristoleate, cetyl oleate, cetyl palmitoleate and cetyl stearate, placed in a formulation at 4-8%.

A third preferred penetrant group for this and similar permeant drugs is cetyl decanoate, cetyl isolaurate, cetyl myristoleate, cetyl oleate, and cetyl palmitoleate, placed in a formulation at 5-9%.

The preferred polar solvents for penetrant groups two and three are propylene glycol with ether ethylene glycol and glycerol (20%) or ethylene glycol and glyceryl monostearate (15%).

Example 2

Transdermal Delivery of Testosterone

Similar delivery characteristics are desired for topical application of testosterone. Testosterone is difficult to enter through the skin due to its chemical properties. Testosterone cypionate, however, is a derivative molecule with water solubility properties but it also has a high partition coefficient.

Our results indicated that the preferred penetrant group for this permeant is cetyl decanoate, cetyl isolaurate, cetyl 2-methoxy-5-hexadecenoate cetyl myristoleate, cetyl Ornithine, cetyl oleate, and cetyl palmitoleate, placed in a formulation at 4-7%. The preferred polar solvent is ethanol, propylene glycol isopropanol or polyethylene glycol (PEG 50) at a concentration of 12%. The desired effect is to provide skin penetration with accumulation of permeant that enters the circulation in small quantities over an extended period after application. The CFEP carrying testosterone enters the skin within a few seconds and carries the testosterone into the capillaries. However, there is also a build up residual testosterone at the site of skin application, which serves as a reservoir, to be absorbed slowly over a period of time.

Example 3

Anti-Arthritic Pain and Other Pain Management Compositions

The composition of the invention provides for the administration of permeants with anti-arthritic properties. A topical application consisting of the cetylated fatty ester complexes in concentrations of 5% to 20% with rubefacients (such as methyl salicylate, menthol and for some variations capsaicin can be applied to affected areas of arthritic patients). The permeants were at concentrations ranging from 1-30%. The carrier formulation consisted of a penetrant group of 8 cetyl fatty esters (4-9%; cetyl decanoate, cetyl laurate, cetyl myristate, cetyl myristoleate, cetyl oleate, cetyl palmitate, cetyl palmitoleate and cetyl stearate) with propylene glycol as the polar solvent (12%), in the described cream base at a pH of 6.5. One variation of carrier formulation is also an anti-inflammatory and is used topically to treat joint pain and musculoskeletal pain and other types of pains in arthritis (Kraemer W J et al. 2004 J Rheumatology 31:767-74; Kraemer W J et al. 2005 J Strength and Conditioning Res 19: 475-80 and Sharan et al. 2009, submitted for publication), The preferred polar solvent is propylene glycol.

Compared with placebo base applications to a control group, the group receiving treatment to the affected area was able to obtain a statistically significant improvement in joint functionality and reduction in pain in a specified area such as neck, lower back, knees, head, and other areas with pain inflammation within 30 minutes of the application. Other rubefacients found to be effective include eucalyptus oil at concentrations of 1% to 5%, and camphor at concentrations of 1-7%.

A second preferred penetrant group for this and similar permeant drugs is cetyl decanoate, cetyl isolaurate, cetyl myristoleate, cetyl oleate, and cetyl palmitoleate, placed in a formulation at 4-9%.

A third preferred penetrant group for this and similar permeant drugs is cetyl decanoate, cetyl isolaurate, cetyl 2-methoxy-5-hexadecenoate cetyl myristoleate, cetyl Ornithine, cetyl oleate, and cetyl palmitoleateplaced in a formulation at 4-9%. The preferred polar solvent for penetrant groups two and three is propylene glycol with glycerol (15%).

Example 4

Neuron Repair, Neuropathic Pain And Fibromyalgia Compositions

The active compounds delivered with the CFEP Complex include targeting neuron repair and regeneration molecules like methylcobalamin, gabapentin, pre-gabalin, alpha lipoic acid, free radical neutralizing agents like alpha lipoic acid, catechins and curcumins, molecules like ketamine which is and has been used as a topical anesthetic, anti-depressants like amitriptyline, nortriptyline and other tricyclic anti-depressants that are useful delivered topically, analgesics like ketoprofen, methyl salicylate, menthol, and camphor and NSAIDs like Diclofenac, and numerous other NSAIDs. Neurogenic inhibitors like capsaicin can also be delivered with the CFEP complex.

Alpha lipoic acid because of its unique solubility in both water and fat permeates well in any of the three formulations above in example 3. Ketamine [2-(2-chlorophenyl)-2-(methylamino)-cyclohexanone] is a water-soluble arylcycloalkylamine with a pKa of 7.5. Its free base, ketamine, has lipid solubility 10 times that of thiopentone (therefore, a cream base with elevated pH is required). Gabapentin is an anticonvulsant also with good water solubility. Oral pregabalin is widely used now in the treatment of neuropathic pain and is also very compatible with our CFEP complex. In our invention, which can be a topical cream, gel, spray, or a transdermal patch, we have used methylcobalamin at a concentration of 0.05% to 5% of methylcobalamin in a permeant cream base containing the penetrant group cetylated fatty esters.

The preferred carrier formulation consisted of a penetrant group of cetyl decanoate, cetyl isolaurate, cetyl 2-methoxy-5-hexadecenoate cetyl myristoleate, cetyl ornithine, cetyl oleate, and cetyl palmitoleate (at a concentration of 5-9%, depending on the permeants) mixed in with the cream base and polar solvent Methylcobalamin in the concentration of 0.05% to 5% was easily solubilized in aqueous phase and mixed into the oil phase of the penetrant mixture to generate the desired emulsion. If capsaicin was included in the formulation, the concentration of capsaicin was 0.001% to 0.025%, For stability of the formulation ascorbic acid and or citric acid or other antioxidants were used in all formulations and curcuminoids were also added as they provide a cooling effectin neuropathic pain. The pH of the final formulation is also adjusted to improve penetration efficiency. The preferred polar solvent is propylene glycol and glycerol at a final concentration of 0.6% to 15% The patch consists of a semipermeable membrane that encloses a bilayer core. The active agent layer contains methylcobalamin and the CFEP penetrant formulation; the push layer contains osmotic agents and excipients. The active agent layer is highly absorbent containing defined quantities of the methylcobalamin in the permeant delivery matrix. An adhesive outer covering maintains patch contact with the skin.

The second preferred penetrant is cetyl decanoate, cetyl laurate, cetyl myristate, cetyl myristoleate, cetyl oleate, cetyl palmitate, cetyl palmitoleate and cetyl stearate at a concentration of 4-9%.

A third preferred preferred penetrant group for this and similar permeant drugs is cetyl decanoate, cetyl isolaurate, cetyl myristoleate, cetyl oleate, and cetyl palmitoleate) placed in a formulation at 4-9%.

When pain caused by neuropathic pain was assessed post treatment with a cream containing methylcobalamin, there was a significant reduction in pain as measured by VAS scale in arms, and legs. The penetrant group helps deliver the methylcobalamin to the damaged neurons and help reduces the pain. The reduction in pain was significant in both arms and legs. Orally administered methylcobalamin although effective in reducing neuropathic pain takes several weeks for efficacy to set in.

In an extension of the above invention in the treatment of diabetic neuropathic pain, post herpetic neuralgia, fibromyalgia, and convulsions, we use pregabalin and gabapentin in a topical cream, gel, spray, or a transdermal patch, at a concentration of 0.01% to 15% of pregabalin or gabapentin in a cream base containing the penetrant group cetylated fatty esters. The formulation can be with or without capsaicin when formulated for neuropathic pain release. The formulation also can contain methylcobalamin and Pregabalin wherein the two molecules acting via different mechanisms of action may provide effective pain relief. This invention could potentially also obviate abuse and dependence on the drug found with oral treatment and also significantly reduce the adverse effects seen in the oral formulations. The preferred carrier formulation for pregabalin or gabapentin with or without capsaicin or in combination with methylcobalamin consisted of a penetrant group of cetyl decanoate, cetyl isolaurate, cetyl 2-methoxy-5-hexadecenoate cetyl myristoleate, cetyl ornithine, cetyl oleate, and cetyl palmitoleate at a concentration of 5-9%, depending on the permeants, mixed in with the penetrant cream base and polar solvent placed in a formulation containing 0.01% to 15% pregabalin or gabapentin; and when methyl cobalamin is also combined with pregabalin, the concentration of methylcobalamin is 0.05% to 5%. When capsaicin was also used its concentration was at 0.001% to 0.025%. These molecules were easily solubilized in aqueous phase and mixed in the oil phase of the penetrant mixture. For stability any antioxidant such as ascorbic acid or citric acid or others were used in all formulations and curcuminoids were also added to soothe inflammation associated with neuropathic pain. The pH of the final formulation is also adjusted to improve penetration efficiency. The preferred polar solvent is propylene glycol and glycerol at a final concentration of 0.6% to 15%. A transdermal patch may be prepared using conventional methods and the pregabalin or gabapentin with or without methylcobalamin and with or without capsaicin dissolved in the cetyl fatty ester pentrant formulation described previously. The patch would have an active agent layer with penetrant matrix, an osmotic push layer and semipermeable membrane held in place with an adhesive layer. The second preferred penetrant for the above invention is cetyl decanoate, cetyl laurate, cetyl myristate, cetyl myristoleate, cetyl oleate, cetyl palmitate, cetyl palmitoleate and cetyl stearate, at a concentration of 4-9%.

A third preferred preferred penetrant group for the above invention and similar permeant drugs is cetyl decanoate, cetyl isolaurate, cetyl myristoleate, cetyl oleate, and cetyl palmitoleate, placed in a formulation at 4-9%.

The above invention can be adapted to a topical cream, gel, lotion, spray or a patch with appropriate CFEP complex to deliver the drugs and molecules.

Example 5

Stick Gel Based Delivery of Pain Compositions

A formulation for transdermal delivery using the CEFP-complex and various rubefacients as described in Example 3 using a sodium stearate based gel stick in a plastic mold, similar to deodorant sticks. Numerous rubefacients such as methyl salicylate, menthol, and camphor in concentrations of 1-30%, individually or in combinations, and with other neurogenic inhibitors such as capsaicin in concentrations of 0.001% to 0.025% either singly or in combination with other rubefacients. The stick gel formulation can also contain vitamin B12 (methylcobalamin) in concentrations of 0.05 to 5% to be used by diabetic patients suffering from neuropathic pain and patients suffering from other forms of neurological pain. Similarly the stick gel formulation can also contain pregabalin with or without methylcobalamin in concentrations of 0.01 to 15% to be used by diabetic patients suffering from neuropathic pain and patients suffering from other forms of neurological pain. The carrier formulation consisted of a penetrant group of 8 cetyl fatty esters (4-9%, cetyl decanoate, cetyl laurate, cetyl myristate, cetyl myristoleate, cetyl oleate, cetyl palmitate, cetyl palmitoleate and cetyl stearate) with propylene glycol as the polar solvent (12%), tocopherol acetate (1%), in the described cream base at a pH of 6.5.

Compared with placebo stick gel applications to a control group, the group receiving treatment to the affected area using stick gel and CFEP-complex and the rubefacients were able to obtain a statistically significant improvement in joint functionality and reduction in pain in a specified area such as neck, lower back, knees, head, and other areas with pain inflammation within 30 minutes of the application.

A second preferred preferred penetrant group for this and similar permeant drugs is cetyl decanoate, cetyl isolaurate, cetyl myristoleate, cetyl oleate, and cetyl palmitoleate, placed in a formulation at 4-9%.

A third preferred penetrant group for this and similar permeant drugs is cetyl decanoate, cetyl isolaurate, cetyl 2-methoxy-5-hexadecenoate cetyl myristoleate, cetyl Ornithine, cetyl oleate, and cetyl palmitoleate, placed in a formulation at 4-9%. The preferred polar solvent for penetrant groups two and three is propylene glycol with glycerol (15%).

The active compounds delivered with the CFEP Complex in a stick gel include targeting neuron repair and regeneration molecules described in Example 4 above, like methylcobalamin, gabapentin, pregaballin, alpha lipoic acid, free radical neutralizing agents like alpha lipoic acid, catechins, or curcumins, molecules like ketamine which is and has been used as a topical anesthetic, anti-depressants like amitriptyline, nortriptyline and other tricyclic anti-depressants that are useful delivered topically, analgesics like ketoprofen, methyl salicylate, menthol, and camphor and NSAIDs like Diclofenac, and numerous other NSAIDs.

Alpha lipoic acid because of its unique solubility in both water and fat permeates well in any of the three formulations above. Ketamine [2-(2-chlorophenyl)-2-(methylamino)-cyclohexanone] is a water-soluble arylcycloalkylamine with a pKa of 7.5. Its free base, ketamine, has lipid solubility 10 times that of thiopentone, therefore, a cream base with elevated pH is required. Gabapentin is an anticonvulsant also with good water solubility.

The preferred carrier formulation consisted of a penetrant group in the stick gel containing cetyl decanoate, cetyl isolaurate, cetyl 2-methoxy-5-hexadecenoate cetyl myristoleate, cetyl Ornithine, cetyl oleate, and cetyl palmitoleate at a concentration of 4-9%, depending on the permeants, mixed in with the permeants cream base and polar solvent at) placed in a formulation at 5-9%. The pH of the final formulation is also adjusted to improve penetration efficiency. The preferred polar solvent is propylene glycol and glycerol at a final concentration of 12%.

The second preferred penetrant in the stick gel is cetyl decanoate, cetyl laurate, cetyl myristate, cetyl myristoleate, cetyl oleate, cetyl palmitate, cetyl palmitoleate and cetyl stearate at a concentration of 4-9%.

A third preferred preferred penetrant group in the stick gel for this and similar permeant drugs is cetyl decanoate, cetyl isolaurate, cetyl myristoleate, cetyl oleate, and cetyl palmitoleate, placed in a formulation at 4-9%.

Example 6

Transdermal delivery of diazepam and other similar agents such as pregabalin for treatment of seizures due to epilepsy and other types of seizures.

A formulation for transdermal delivery is a novel format for diazepam or lorazepam or clonazepam, and utilizes the lipophilic properties of each molecule. In one example diazepam is administered in 3 doses, namely 10 mg/gram, 25 mg/gram and 50 mg/gram using a 4-9% CFEP-Complex carrier formulation consisting of cetyl decanoate, cetyl laurate, cetyl myristate, cetyl myristoleate, cetyl oleate, cetyl palmitate, cetyl palmitoleate and cetyl stearate. The polar solvent used is propylene glycol (12%) in the described cream base at a pH of 6.5. A pH range of 6-7 is effective and tocopherol acetate is the antioxidant at 1%. Preliminary results show that a therapeutic dose can be administered using the combinations indicated above. The permeant is first finely emulsified in the CFEP-Complex and polar solvent prior to addition of the cream base. A single application of diazepam delivered to mouse skin in this formulation may provide pronounced activity for 5-8 hours. Transdermal delivery is also pronounced significantly with addition of urea and a non-ionic surfactant. Pregabalin in a topical format is also an excellent anti-convulsant and useful in the treatment of seizure already described in examples 4 and 5 above.

A second preferred penetrant group for this and similar permeant drugs is cetyl 13-methyl myristate, cetyl myristate, cetyl oleate, cetyl ornithine, cetyl palmitoleate and cetyl stearate, placed in a formulation at 4-9%. The preferred polar solvent is propylene glycol and glycerol at a final concentration of 12%. The second preferred polar solvent is isopropanol and propylene glycol at 12%. This formulation may be more effective with clonazepam.

A third preferred preferred penetrant group for this and similar permeant drugs is cetyl decanoate, cetyl myristate, cetyl oleate, cetyl ornithine and cetyl palmitoleate, placed in a formulation at 4-9%. The preferred polar solvent is propylene glycol and glycerol at a final concentration of 12%. This formulation may be more effective with lorazepam.

Example 7

Anti-Wrinkle and Anti-Aging Cream and Gel

A topical application consisting of restorative and protective permeants (such as dimethicone, white curcumin, small peptides, cyclopentasiloxane) was applied to face and neck twice per day. The permeants were at concentrations ranging from 0.4-9%. The carrier formulation consisted of a penetrant group of 8 cetyl fatty esters (4-9%; cetyl decanoate, cetyl laurate, cetyl myristate, cetyl myristoleate, cetyl oleate, cetyl palmitate, cetyl palmitoleate and cetyl stearate) with propylene glycol as the polar solvent (15%) along with tocopherol acetate (1%), in the described cream base at a pH of 6.5. A second preferred penetrant group for this and similar permeants is cetyl decanoate, cetyl isolaurate, cetyl 2-methoxy-5-hexadecenoate cetyl myristoleate, cetyl Ornithine, cetyl oleate, and cetyl palmitoleate, placed in a formulation at 4-9%.

Twenty eight female and eight male subjects were studied for 71 days (average age of the group: 44 years). The applications resulted in statistically significant improvements in skin firmness, skin elasticity with reductions in the number and depth of wrinkles. The carrier formulation was found to be well tolerated with no skin irritation.

The formulation facilitates delivery of permeants to the skin in a manner that retains permeants in the skin to provide improvements in skin properties. The data in Table 3 demonstrate that statistical improvements in facial firmness can be observed as early as 28 days of treatment applied twice each day.

TABLE 3

| Facial Firmness - Dermatologist Review | |
|---|---|
| Days of Evaluation | Evaluator Index (mean values) |
| Day 0 | 3.00 |
| Day 28 | 2.33 |
| Day 56 | 2.0 |
| Day 71 | 2.0 |

*n = 30, Difference significance between Day 71 and baseline, p < 0.001

Another feature noted in Table 4 would indicate that the formulation facilitates in administering permeants to affect other skin properties in a beneficial manner.

TABLE 4

| Facial Skin Elasticity (R7 parameter) | |
|---|---|
| Days of Evaluation | R 7 Values (mean) |
| Day 0 | 0.33 |
| Day 28 | 0.39 |
| Day 56 | 0.41 |
| Day 71 | 0.41 |

*n = 30, Difference significance between Day 71 and baseling, p < 0.001

Example 8

Hyperkeratosis and Xerosis

The administration of permeant agents to provide restorative and protective properties to the skin is given in another example. In this example the permeants 10% urea and 1% dimethicone are delivered in an acidic cream formulation with additional emoluents, preferred antioxidants and hemectants. The carrier formulation consisted of a penetrant group of 8 cetyl fatty esters (4-9%; cetyl decanoate, cetyl laurate, cetyl myristate, cetyl myristoleate, cetyl oleate, cetyl palmitate, cetyl palmitoleate and cetyl stearate) with propylene glycol, glyceryl monostearate, cetostearyl alcohol and glycerin at a concentration of 15%. The preferred cream base has a pH of 3-4, which demonstrates the effectiveness of the permeant groups at a low pH, as depicted below in Table 5 below for Permeant and Penetrant treated (P&PT) groups.

TABLE 5

Treatment Differences as Seen Through Changes in the Xerosis Grade.

| | | | | \multicolumn{5}{c}{XEROSIS GRADE (Feet only)} | | | | |
|---|---|---|---|---|---|---|---|---|
| Sex | Age | Diabetic | Start Date | Initial | 2 weeks | 4 weeks | 6 weeks | 8 weeks |
| \multicolumn{9}{c}{Permeant & Penetrant Treated Group} |
| F | 59 | Y | July 01, 2006 | 3 | 2 | 2 | 1 | 1 |
| F | 50 | Y | July 02, 2006 | 2 | 1 | 1 | 0 | 0 |
| F | 64 | N | July 15, 2006 | 3 | 3 | 2 | 2 | 1 |
| F | 60 | Y | July 13, 2006 | 2 | 1 | 0 | 0 | 0 |
| F | 54 | N | July 13, 2006 | 1 | 0 | 0 | 0 | 0 |
| F | 49 | N | July 23, 2006 | 2 | 1 | 0 | 0 | 0 |
| M | 48 | N | July 25, 2006 | 2 | 1 | 1 | 0 | 0 |
| M | 39 | N | July 25, 2006 | 2 | 1 | 1 | 0 | 0 |
| F | 31 | N | July 30, 2006 | 2 | 1 | 0 | 0 | 0 |
| F | 38 | Y | July 29, 2006 | 3 | 2 | 2 | 1 | 1 |
| F | 56 | Y | July 16, 2006 | 1 | 1 | 0 | 0 | 0 |
| F | 50 | N | Aug. 01, 2006 | 3 | 3 | 2 | 2 | 1 |
| F | 59 | N | Aug. 01, 2006 | 2 | 1 | 0 | 0 | 0 |
| M | 48 | Y | Aug. 02, 2006 | 2 | 1 | 0 | 0 | 0 |
| F | 38 | N | Aug. 01, 2006 | 2 | 1 | 1 | 0 | 0 |
| M | 29 | N | Aug. 07, 2006 | 2 | 1 | 1 | 0 | 0 |
| M | 28 | N | Aug. 03, 2006 | 2 | 1 | 0 | 0 | 0 |
| M | 29 | N | Aug. 03, 2006 | 3 | 2 | 2 | 1 | 1 |
| F | 35 | Y | Aug. 05, 2006 | 2 | 1 | 1 | 0 | 0 |
| F | 34 | N | Aug. 05, 2006 | 1 | 0 | 0 | 0 | 0 |
| F | 26 | N | Aug. 01, 2006 | 1 | 0 | 0 | 0 | 0 |
| F | 58 | Y | Aug. 08, 2006 | 2 | 1 | 0 | 0 | 0 |
| F | 26 | N | Aug. 08, 2006 | 2 | 1 | 0 | 0 | 0 |
| F | 19 | N | Aug. 14, 2006 | 1 | 0 | 0 | 0 | 0 |
| M | 42 | N | Aug. 14, 2006 | 2 | 1 | 1 | 0 | 0 |
| F | 36 | N | Aug. 16, 2006 | 1 | 0 | 0 | 0 | 0 |
| M | 55 | Y | Aug. 16, 2006 | 3 | 3 | 3 | 2 | 1 |
| M | 41 | N | Aug. 17, 2006 | 1 | 0 | 0 | 0 | 0 |
| F | 27 | N | Aug. 13, 2006 | 2 | 1 | 0 | 0 | 0 |
| M | 46 | NA | Aug. 17, 2006 | 2 | 1 | 1 | 0 | 0 |
| F | 29 | N | Aug. 14, 2006 | 3 | 3 | 2 | 2 | 1 |
| | | | Sum | 62 | 36 | 23 | 11 | 7 |
| Mean | 42.032 | 9 Diabetic | Mean | 2.000 | 1.161 | 0.742 | 0.355 | 0.226 |
| St Dev | 12.51262 | | St Dev | 0.68313 | 0.89802651 | 0.893224195 | 0.709384104 | 0.42502372 |
| | | | St Error | 0.122645 | 0.161225585 | 0.16036341 | 0.127358008 | 0.07630587 |
| \multicolumn{9}{c}{Placebo Treated Group} |
| F | 52 | N | Aug. 01, 2006 | 3 | 3 | 3 | 3 | 3 |
| F | 29 | N | Aug. 03, 2006 | 2 | 2 | 2 | 2 | 1 |
| F | 41 | N | Aug. 03, 2006 | 2 | 2 | 2 | 2 | 2 |
| F | 23 | N | Aug. 03, 2006 | 2 | 2 | 2 | 2 | 1 |
| M | 36 | Y | Aug. 06, 2006 | 3 | 3 | 3 | 2 | 2 |
| F | 33 | N | Aug. 07, 2006 | 1 | 1 | 1 | 1 | 1 |
| F | 31 | N | Aug. 09, 2006 | 2 | 2 | 2 | 2 | 2 |
| F | 41 | NA | Aug. 08, 2006 | 1 | 1 | 1 | 1 | 0 |
| F | 25 | N | Aug. 10, 2006 | 2 | 2 | 2 | 2 | 1 |
| F | 35 | N | Aug. 13, 2006 | 3 | 3 | 3 | 3 | 3 |
| | | | Sum | 21 | 21 | 21 | 20 | 16 |
| Mean | 34600 | 1 Diabetic | Mean | 2.100 | 2.100 | 2.100 | 2.000 | 1.600 |
| St Dev | 8.566083 | | St Dev | 0.737865 | 0.737864787 | 0.737864787 | 0.666666667 | 0.96609178 |
| | | | St Error | 0.233502 | 0.233501515 | 0.233501515 | 0.210970464 | 0.30572525 |

Thirty-two patients with severe hyperhydrosis and cracking of the cornified skin of the feet were treated with the above formulation with applications twice a day for 8 weeks. Fifteen volunteers were given a placebo cream base without the permeants or the penetration group of cetylated fatty esters. The condition of foot skin was evaluated using a xerosis severity index of 0 to 3 with 0 being normal skin and 3 being severe xerosis (large scale plates with fissures, often characterized as deep and erythematous).

Results show that even as early as week 2, a statistically significant difference was noted between the Permeant and Penetrant groups versus the Placebo group in regards to severity of xerosis. Xerosis mean index in the study group reduced dramatically while essentially no change in mean severity index was found with the placebo group. The change in mean severity index for the Permeant and Penetrant treated group continued to show improvements in that group with each successive week of treatment. Although the rate of change slowed after the $4^{th}$ week, a 36.4% change in mean values was still noted between the $6^{th}$ and $8^{th}$ week. At each week of evaluation, the mean index values for the treated group showed statistically significant improvements compared with the placebo group, which only showed some change by week 8 (attributed to application of the base cream to the foot). The average score for the P&PT group went from a moderate index value of 2.00 to a value of 0.23 (mild to almost normal) by the end of 8 weeks. The placebo group had a mean value of 1.6 (mild to moderate) by week 8.

REFERENCES

1. Gale, awarded on Jan. 29, 2008 U.S. Pat. No. 7,323,191, for Transdermal warfarin system describes composition of matter for application to a body surface or membrane to administer warfarin by permeation through the body surface or membrane.
2. Jordan, awarded on Jan. 8, 2008 U.S. Pat. No. 7,316,820, for transdermal delivery system and relates to the discovery of a transdermal delivery system that can deliver high molecular weight pharmaceuticals and cosmetic agents to skin cells.
3. Compounds which are generally IP receptor antagonists can be traced to Cournoyer, et al. in U.S. Pat. No. 7,312,230 entitled Carboxylic acid derivatives as IP antagonists, awarded on Dec. 25, 2007.
4. A transdermal delivery system (TDS) which may be applied as an open (liquid, gel) or closed (patch) article that rapidly crosses the skin barrier can be traced to Kirby, et al. in U.S. Pat. No. 7,267,829 entitled 'Compositions for rapid and non-irritating transdermal delivery of pharmaceutically active agents' awarded on Sep. 11, 2007.
5. The art of "preparing a two-phase water-absorbent bioadhesive composition", discloses a method for preparing a composition that contains both a hydrophobic phase and a hydrophilic phase, contributed by U.S. Pat. No. 7,138,458 issued to Cleary, et al. on Nov. 21, 2006
6. Chong, awarded on Aug. 28, 2007 U.S. Pat. No. 7,262,224 for Cosmetic rejuvenating and healing product, method of its manufacture and uses thereof, and describes a cosmetic composition for rejuvenating the appearance of skin.
7. U.S. Pat. No. 7,182,955, awarded for invention of "Abuse-resistant transdermal dosage form" describes an active agent component an abusable drug substance, an overlay backing, a porous material, and an antagonist reservoir to Hart, et al. on Feb. 27, 2007.
8. U.S. Pat. No. 6,946,144 entitled Transdermal delivery system, awarded to Jordan on Sep. 20, 2005 relates to the discovery of a transdermal delivery system that can deliver high molecular weight pharmaceuticals and cosmetic agents to skin cells.
9. Changaris, awarded on Jul. 11, 2006 U.S. Pat. No. 7,074,418 entitled 'Conjugated fatty acid based emulsion and methods for preparing and using same', describes diene conjugated fatty acids which are also useful as a carrier and delivery vehicle of the macromolecules.
10. "An anti-inflammatory analgesic gel composition", can be traced to Noda, et al. in U.S. Pat. No. 4,393,076, entitled 'Anti-inflammatory and analgesic gel composition' awarded on Jul. 12, 1983.
11. U.S. Pat. No. 4,808,414 entitled "Amide penetration enhancers for transdermal delivery of systemic agents" awarded to Peck, et al. on Feb. 28, 1989, describes topically administering with a said systemic agent an effective amount of a membrane penetration enhancer.
12. "A Method for the treatment of osteoarthritis" by Diehl, described for alleviating the symptoms of non-rheumatoid arthritis by administering cetyl myristoleate either orally, topically, or parenterally, was awarded U.S. Pat. No. 5,569,676 on Oct. 29, 1996.
13. Discovery that by simultaneously administering particular dosage levels by means of a transdermal delivery system, anesthesia may be induced in patients, can be traced to U.S. Pat. No. 5,635,204, entitled 'Method for transdermal induction of anesthesia, analgesia or sedation' awarded to Gevirtz, et al. on Jun. 3, 1997.
14. U.S. Pat. No. 5,646,151, entitled "Kappa agonist compounds and pharmaceutical formulations thereof" describes, compounds, compositions and method of treating hyperalgesia comprising a compound as defined in the specification awarded to Kruse, et al. on Jul. 8, 1997.
15. Disclosed are topical compositions which provide good coverage of skin imperfections, in U.S. Pat. No. 5,972,359, entitled skin care compositions and methods of improving skin appearance awarded to Sine, et al. on Oct. 26, 1999.
16. An invention which comprises of a cream type carrier for topical delivery of medicaments including analgesics is described in U.S. Pat. No. 6,461,600, entitled "Topical pain relief composition and carrier", awarded to Ford on Oct. 8, 2002.
17. 'Topical compositions and methods for treating pain' describes an invention that induces a local-anesthetic effect when topically administered to intact skin, in U.S. Pat. No. 6,638,981, awarded to Williams, et al. on Oct. 28, 2003.
18. Levin, awarded U.S. Pat. No. 7,112,578 on Sep. 26, 2006 entitled Methods and compositions for treatment of inflammatory disease describes Compositions useful for treating inflammatory diseases including arthritis are disclosed which comprise cetyl myristoleate compounds.
19. U.S. Pat. No. 4,049,824, awarded to Diehl on Sep. 20, 1977, entitled Cetyl myristoleate, describes a method for immunizing against inflammatory rheumatoid arthritis in mammals.
20. 'Methods of delivery of cetyl myristoleate' provides delivery devices for compositions of cetyl myristoleate, including transdermal delivery devices, suppositories, enteric coatings, and microencapsulation, in U.S. Pat. No. 6,417,227, awarded to Lord, et al. on Jul. 9, 2002.
21. U.S. Pat. No. 7,223,877, awarded to Leonard on May 29, 2007, entitled uses of hydroquinone substituted polyunsaturated fatty acids as antioxidants, relates to the use of fatty acids as antioxidants.

World Patent References

22. "SYNTHESIS OF ESTER LINKED LONG CHAIN ALKYL MOIETIES' provides a process for preparing a mixture of cetyl myristate and cetyl palmitate, in world patent WO03018731, awarded, on Mar. 6, 2003 to CADWALLADER DIANNE (NZ); JHAVERI PARAG (IN)
23. "Pharmaceutical carriers and compositions for transdermal drug delivery" unfolds a skin permeation enhancing agent & a surface adhesion molecule acting in synergy, in world patent WO0211784, also published as WO0211784 (A3) on Feb. 14, 2002, awarded to HERZBERG MAX (IL); MESSIKA ERIC (IL); GHOZI MICHAL (IL)
24. SUNAMOTO JIYUNZOU; IWAMOTO KIYOSHI, awarded patent JP58049311, entitled preparation of stable liposome, describes the prevention of destruction of liposome by covering it with an ester of polysaccharide and fatty acid.
25. HOYT KENNETH (US); LEMLEY PAUL (US), awarded WO9833474, on Aug. 6, 1998, entitled USE OF OIL FROM EMU OR RHEA BIRDS AS TRANS-MEMBRANE CARRIERS FOR DELIVERY OF DRUGS, PEPTIDES AND VACCINES, describes a method for transdermal transportation of proteins, peptides using oil obtained from the sebaceous glands of rhea and emu birds.
26. "Transdermal carrier materials", awarded EP0038512, on Oct. 28, 1981 to SCHAFER WERNER; SCHAFER ROLF DR; SCHAFER DORIS DR for describing use of amphoteric ionic complexes as effective carriers for active pharmaceutical or cosmetic ingredients.
27. WEISMAN, Bernard, awarded WO119981052583, on Nov. 26, 1998, entitled, NATURAL COMPOSITION FOR TREATING BONE OR JOINT INFLAMMATION, describes a novel composition for treating conditions characterized by bone or joint inflammation with cetyl myristoleate Academic References:

28. Skin Care and Cosmetic Ingredients Dictionary, p. 243 (1994). "Handbook of Pharmaceutical Excipients," Edited by Arthur H. Kibbe, Ph.D., Am. Pharm. Assoc., 3:292-294, 2000.
29. "Cardinal Manifestations and Presentations of Diseases," Hesslink R, Armstrong D, Nagendran M V, Sreevatsan S, Barathur R (2002)
30. Cetylated fatty acids improve knee function in patients with osteoarthritis. J Rheumatol 29:1708-12.
31. Kraemer W J, Ratamess N A, Maresh C M, Anderson J A, et al. (2005) Fatty Acid Topical Cream with Menthol Reduces Pain and improves functional performance in individuals with osteoarthritis. J Strength and Conditioning Res 19(2): 475-480.
32. Diehl H W, May E L. Cetyl myristoleate isolated from swiss albino mice: an apparent protective agent against adjuvant arthritis in rats. J Pharm Sci 1994; 83:296-9.
33. Kraemer W J, Ratamess N A, Maresh C M, Anderson J A, et al. (2005) Effects of treatment with a cetylated fatty acid topical cream on static postural stability and plantar pressure distribution in patients with knee osteoarthritis. J Strength and Conditioning Res 19(1): 115-121.
34. Vinik A. Diagnosis and management of diabetic neuropathy. Clin Geriatric Med 1999; 15:293-297.
35. Fedele D, Giugliano D. Peripheral diabetic neuropathy: Current recommendations and future prospects for its prevention and management. Drugs 1997; 54:414-420.
36. Diabetes Control and Complications Trial Research Group. The effect of intensive diabetes therapy on the development and progression of neuropathy. Ann Intern Med 1995; 122:561-568.
37. Galer B S. Neuropathic pain of peripheral origin: Advances in pharmacologic treatment. Neurology 1995; 45(Suppl 9):17-24.
38. Nadine A, Bouhassira D. Mechanisms of pain in peripheral neuropathy. Acta Neurol Scand 1999; (Supp 173):12-24.
39. Benbow S J, Cossins L, MacFarlane I A. Painful diabetic neuropathy. Diabet Med 1999; 16:632-644.
40. Serra J. Overview of neuropathic pain syndromes. Acta Neurol Scand 1999; (suppl 173):7-11.
41. Emanuele N V, Emanuele M A. Drugs to treat the tissue complications of diabetes: Peripheral neuropathy. Comprehensive Therapy 1995; 21:579-582.
42. Kingery W S. A critical review of controlled clinical trials of peripheral neuropathic pain and complex regional pain syndromes. Pain 1997; 73:123-139.
43. Lipman A G. Analgesic drugs for neuropathic and sympathetically maintained pain. Clin Geriatric Med 1996; 12:501-514.
44. Bonezzi C, Demartini L. Treatment options in postherpetic neuralgia. Acta Neurol Scand 1999; (Suppl 173):25-28.
45. Crowley K L, Flores J A, Hughes C N et al. Clinical application of ketamine ointment in the treatment of sympathetically maintained pain. International Journal of Pharmaceutical Compounding 1998; 2:122-127. Anesthesiology, 71:178-187 (1989).
46. Ibid Anesthesiology, 70:928-934 (1989).
47. Anesthesiology, 64:36-42 (1986). Harrison's Principles of Internal Medicine, Edited by A. Fauci et al., 14:1:53-58, 1998.
48. T. Ghosh et al., Transdermal and Topical Drug Delivery Systems, "Types of Dermal Drug Delivery," Interpharm Press, Inc., p. 7, 1997.
49. T. Ghosh et al., Transdermal and Topical Drug Delivery Systems, "Transdermal and Dermal Therapeutic Systems," Interpharm Press, Inc., pp. 87-93, 1997.
50. "Percutaneous Absorption," edited by R. Bronaugh et al., 2.sup.nd Ed., 1369 Contents, 1989.
51. Zurier, R. B. 1993. Fatty acids, inflammation and immune response. Prostaglandins Leukot. Essent. Fatty Acids. 48: 57-62.
52. Van der Heide, J. J., H. J. Biol, J. M. Donker, J. M. Wilmink, and A. M. Tegzess. 1993. Effect of dietary fish oil on renal function and rejection in cyclosporine-treated recipients of renal transplants. N. Engl. J. Med. 329: 769-773.
53. Curtis, C. L., Hughes, C. E., Flannery, C. R., Little, C. B., Harwood, J. L., and Caterson, B. (2000) J. Biol. Chem. 275, 721-724.
54. Ashe, B. M., and Zimmerman, M. (1977) Biochem. Biophys. Res. Commun. 75, 194-199
55. Tyagi, S. C., and Simon, S. R. (1991) J. Biol. Chem. 266, 15185-15191
56. Higazi, A. A.-R., Finci-Yeheskel, Z., Samara, A. A.-R., Aziza, R., and Mayer, M. (1992) Biochem. J. 282, 863-866
57. Higazi, A. A.-R., Aziza, R., Samara, A. A.-R., and Mayer, M. (1994) Biochem. J. 300, 251-255
58. Serhan C N, et al. Novel functional sets of lipid-derived mediators with anti-inflammatory actions generated from omega-3 fatty acids via cyclooxygenase 2-nonsteroidal anti-inflammatory drugs and transcellular processing. J Exp Med 2000 October; 192(8):1197-204.
59. Perez-Jimenez F, Castro P, Lopez-Miranda J, et al. (2002) Circulating levels of endothelial function are modulated by dietary monounsaturated fat. Atherosclerosis 145: 351-358.
60. Calder P C, Yagoob P, Thies F, Wallace F A, Miles E A. Fatty acids and lymphocyte functions. Br J Nutr 87(1): S31-48, 2002.

61. Mata P, Alonso R, Lopez-Miranda J, et al. Effect of dietary fat saturation on LDL oxidation and monocyte adhesion to human endothelial cells in vitro. Arterioscler Thromb Vasc Biol 16: 1347-1355, 1996.
62. Perez-Jimenez F, Castro P, Lopez-Miranda J, et al. Circulating levels of endothelial function are modulated by dietary monounsaturated fat. Atherosclerosis 145: 351-358, 1999
63. Vicennati V, Vottero A, Friedman C, Papanicolaou D A. Hormonal regulation of interleuki-6 production in human adipocytes. Int J Obes Relat Metab Disord 26(7): 905-911, 2002.
64. Zaloga G P, Marik P. Lipid modulation and systemic inflammation. Crit Care Clin 17(1): 201-217, 2001.
65. De Caterina, et al. (00) Am J Clin Nutr 71(suppl): 213s-23s
66. Diehl H W, May E L. Cetyl myristoleate isolated from swiss albino mice: an apparent protective agent against adjuvant arthritis in rats. J Pharm Sci 1994; 83:296-9.
67. Iguchi K, Okumura N, Usui S, Sajiki H, Hirota K, Kiran K. Myristoleic acid, a cytotoxic component in the extract from serenoa repens, induces apoptosis and necrosis in human prostatic LNCaP cells. Prostate 2001; 47:59-65.
68. Bonnet C, Bertin P, Cook-Moreau J, Chable-Rabinovitch H, Treves R, Rigaud M. Lipoxygenase products and expression of 5-lipoxygenase and 5-lipoxygenase-activating protein in human cultured synovial cells. Prostaglandins 1995; 50:127-35.
69. Kishore N S, et al. Comparison of the acyl chain specificities of human myristoyl-CoA synthetase and human myristoyl-CoA:protein N-myristoyltransferase. J Biol Chem 1993; 268(7):4889-902.
70. Iguchi K, et al. Myristoleic acid, a cytotoxic component in the extract from Serenoa repens, induces apoptosis and necrosis in human prostatic LNCaP cells. Prostate 2001; 47:59-65.
71. Raju R, et al. Mammalian myristoyl Co:A protein N-myristoyltransferase. MolCell Biochem 1995; 149/150: 191-202.
72. Zeyda M, Staffler G, Horejsi V, Waldhausl W, Stulnig T M. LAT Displacement from Lipids Rafts as Molecular Mechanism for Inhibition of T Cell Signaling by Polyunsaturated Fatty Acids. J Biol Chem. August 9; 277(32):28418-23, 2002.]
73. Yao Y, Eshun J K, Lu S, Berschneider H M, Black D D. Regulation of triacylglycerol and phospholipid trafficking by fatty acids in newborn swine enterocytes. Am J Physiol Gastrointest Liver Physiol 282: G817-824, 2002.
74. Hornung B, Amtmann E, Sauer G. Lauric acid inhibits the maturation of vesicular stomatitis virus. Journal of General Virology 1994; 75:353-361.
75. Hierholzer, J. C. and Kabara, J. J. In vitro effects of monolaurin compounds on enveloped RNA and DNA viruses. Journal of Food Safety 1982; 4:1-12.
76. Projan S J, Brown-Skrobot S, Schlievert P M, Vandenesch F, Novick R P. Glycerol monolaurate inhibits the production of beta-lactamase, toxic shock toxin-1, and other staphylococcal exoproteins by interfering with signal transduction. Journal of Bacteriology. 1994; 176:4204-4209.
77. Anonymous. How monounsaturates may save arteries. Science News 1443 Jun. 9, 1990:367.
78. Curtis, C. L., Hughes, C. E., Flannery, C. R., Little, C. B., Harwood, J. L., and Caterson, B. (2000) J. Biol. Chem. 275, 721-724
79. Ashe, B. M., and Zimmerman, M. (1977) Biochem. Biophys. Res. Commun. 75, 194-199
80. Tyagi, S. C., and Simon, S. R. (1991) J. Biol. Chem. 266, 15185-15191
81. Qiurong Li*, Meng Wang*, Li Tan*, Chang Wang, et al. Docosahexaenoic acid changes lipid composition and interleukin-2 receptor signaling in membrane rafts. Journal of Lipid Research, Vol. 46, 1904-1913, September 2005
82. Kraemer W J, Ratamess N A, Maresh C M, Anderson J A, et al. (2005) Fatty Acid Topical Cream with Menthol Reduces Pain and improves functional performance in individuals with osteoarthritis. J Strength and Conditioning Res 19(2): 475-480.
83. Cochran C and Dent R: (1997) Cetyl myristoleate—a unique natural compound valuable in arthritis conditions. From Townsend Newsletter for Doctors and Patients July.
84. Siemandi H. (1997) The effect of cis-9-myristoleate (CMO) and adjunctive therapy on arthritis and autoimmune disease—a randomized trial. Townsend Letter for Doctors & Patients August/September:58-63.
85. Hesslink R, Armstrong D, Nagendran M V, Sreevatsan S, Barathur R (2002) Cetylated fatty acids improve knee function in patients with osteoarthritis. J Rheumatol 29:1708-12.
86. Kraemer W J, Ratamess N A, Maresh C M, Anderson J A, et al. (2005) Effects of treatment with a cetylated fatty acid topical cream on static postural stability and plantar pressure distribution in patients with knee osteoarthritis. J Strength and Conditioning Res 19(1): 115-121.
87. Rajala R V, Datla R s, Moyana T N, et al. (2000) N-myristoyltransferase. Mol. Cell Biochem 204: 135-55.

The invention claimed is:

1. A transdermal delivery composition containing one or more active agents in a carrier comprising:
   a) four or more cetylated compounds in combinations best suited for the permeation of said active agent through the skin; said cetylated compounds are present at a combined concentration ranging from 4-20% and are selected from the group consisting of cetyl arginine, cetyl 11-cyclohexylundecanoate, cetyl decanoate, cetyl dihomo-y-linolenate, cetyl docosapentanoate, cetyl eicosapentanoate, cetyl isolaurate, cetyl isomyristate, cetyl laurate, cetyl linolenate, cetyl 2-methoxy-5-hexadecenoate, cetyl 13-methyl myristate, cetyl myristoleate, cetyl myristate, cetyl oleate, cetyl ornithine, cetyl palmitate, cetyl palmitoleate, cetyl stearate, cetyl stearidonate and cetyl vaccenate; and
   b) one or more polar solvents present in combined concentrations ranging from 5-30%, wherein the solvents are selected from the group consisting of 1,2,4-butane triol, dimethicone copolyol, ethanol, ethylene glycol, glycerol, glyceryl monostearate, 1,2,6-hexane triol, isopropanol, polyethylene glycol and propylene glycol;
   Wherein said cetylated compounds and polar solvents are of suitable combinations so as to provide effective transdermal delivery of the active agent.

2. The transdermal delivery composition of claim 1 wherein the one or more polar solvents comprises a polyethylene glycol selected from the group consisting of PEG 50, PEG 100, PEG 500 and PEG 100 Stearate.

3. The transdermal delivery composition of claim 1 wherein the pH of said composition ranges from 4 to 10 in order to provide the best permeation of the active agent.

4. The transdermal delivery composition of claim 1 wherein said composition is in the form of a cream, gel, lotion, patch, solid gel or stearate based stick gel.

5. The transdermal delivery composition of claim 4, wherein the active agent is an antioxidant, an analgesic or a cosmeceutical compound.

6. The transdermal delivery composition of claim 1, wherein the one or more active agent is selected from the group consisting of oxybutynin, tolteridone and combinations thereof, for use in the treatment of urinary incontinence or overactive bladder.

7. The transdermal delivery composition of claim 1, wherein the active agent is testosterone for use in treatment of testosterone deficiency.

8. The transdermal delivery composition of claim 1, wherein the one or more active agents are selected from the group consisting of valproate, phenyloin, thiopentone, pentobarbital, propofol, isoflurane, felbamate, midazolam, diazepam, clobazam, folinic acid, pyridoxine, gabapentin, vigabatrin and combinations thereof, for use in the treatment of seizures.

9. The transdermal delivery composition of claim 1, wherein the one or more active agents are selected from the group consisting of diclofenac, naproxen, non-steroidal anti-inflammatory drugs (NSAIDs), rubifacients, analgesics and combinations thereof, for use in the treatment of joint pain, musculoskeletal pain or arthritic pain.

10. The transdermal delivery composition of claim 1, wherein the one or more active agents are selected from the group consisting of a vitamin, catechin, curcumin and combinations thereof.

11. The transdermal delivery composition of claim 1, wherein the one or more active agents is methylcobalamin.

12. A method of using the transdermal delivery composition of claim 9 for the treatment of pain associated with peripheral neuropathies in diabetics or other neuropathic pain disorders, and non-neuropathic pain, comprising topically applying the transdermal delivery composition of claim 9 in or around the site of pain.

13. The transdermal delivery composition of claim 1, wherein the one or more active agents are selected from the group consisting of gabapentin, ketamine, pregabalin, nortriptyline, amitriptyline and combinations thereof, for use in the treatment of pain associated with peripheral neuropathies in diabetics or other neuropathic pain disorders, or non-neuropathic pain.

14. The transdermal delivery composition of claim 1, wherein the one or more active agents are selected from the group consisting of exfoliating agents, debriding agents and combinations thereof, for use in the treatment of cracked and dry skin due to hyperkeratosis and xerosis.

15. The transdermal delivery composition of claim 1, wherein the one or more active agents are selected from the group consisting of small peptides, protein based serums, antioxidants, silicones, co-polymers or elastomers and combinations thereof, for use in the treatment of skin conditions and for skin firming.

16. The transdermal delivery composition of claim 15, wherein the antioxidants are selected from alpha lipoic acid and curcumin, and the silicones are selected from cyclopentasiloxanes.

17. The transdermal delivery composition of claim 1, wherein the one or more active agents are selected from the group consisting of one or more soluble pollen allergens, for use in allergen immunotherapy.

* * * * *